Sept. 24, 1963 T. B. KYLE Plant Pat. 2,286

ASH TREE

Filed Aug. 8, 1961

INVENTOR.
THOMAS B. KYLE

BY William R Jacox
ATTORNEY

United States Patent Office

Plant Pat. 2,286
Patented Sept. 24, 1963

2,286
ASH TREE

Thomas B. Kyle, Tipp City, Ohio, assignor to Spring Hill Nurseries Company, Tipp City, Ohio, a corporation of Ohio Filed Aug. 8, 1961, Ser. No. 130,203
1 Claim. (Cl. Plt.—51)

This invention relates to a new and distinct variety of ash tree. The new tree was discovered by me near Tipp City, Ohio, in a cultivated area.

It is believed that the tree is an unknown seedling. I have propagated my new variety of ash tree at Tipp City, Ohio, asexually by budding and the characteristics herein noted have proved to be firmly fixed in the progeny.

The most distinguishing characteristics of my new ash tree are the light green foliage, which turns golden yellow during late summer and fall, and the young branches and twigs which are a smooth golden yellow color, providing an interesting contrast to the usual green leaves and darker bark of most other trees. While most ash trees shed their leaves rapidly in the fall, giving little, if any show of autumn color, my new ash changes color during late August and retains its golden foliage until leaf drop several months later.

One of the undesirable characteristics of ash trees is the habit of producing large clusters of winged key or samara fruit which ultimately drop and litter the ground under the trees. My new ash has developed to maturity and is definitely sterile and will not develop fruit.

The tree grows rapidly when young, is compact and broad headed, and medium in height, making a fine tree for street and lawn planting.

Figure 1:
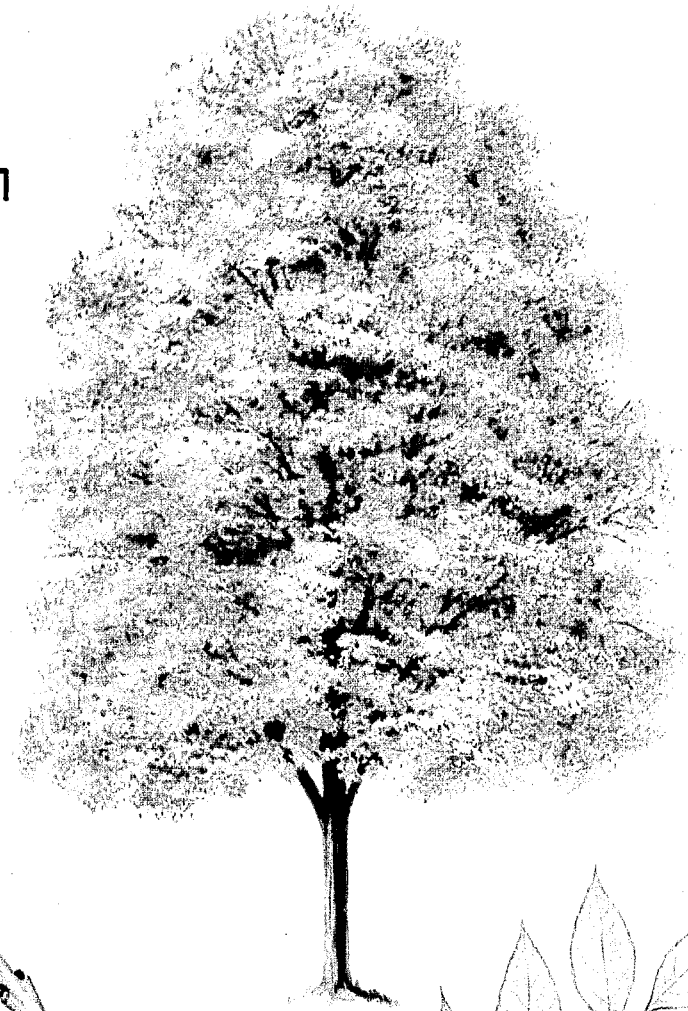
FIG. 1 shows a mature specimen of my new ash tree with the coloration produced in late summer and fall.
Figure 3:
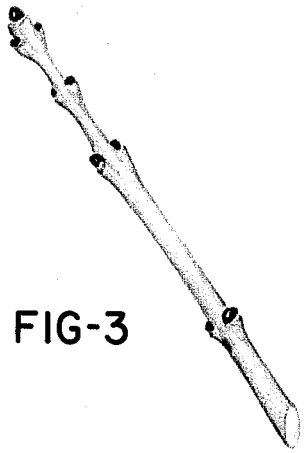
FIG. 3 shows the bark as it appears on the younger branches and on the new growth of the tree.
Figure 2:
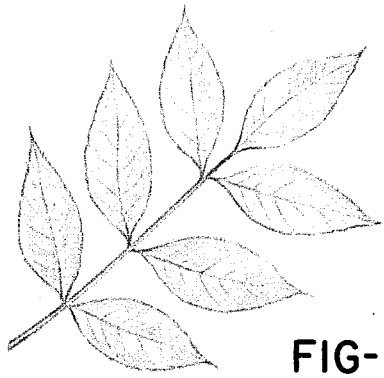
FIG. 2 is an illustration of one of the compound leaves with the coloration produced in late summer and fall.

Following is a brief detailed description of my new variety with color reference numbers and letters in accordance with Color Harmony Manual of Container Corporation of America, edited by Taylor, Knocke, and Granville:

Tree: Durable, hardwood, with a distinctive rounded top.

Growth: Rapid and vigorous, of medium size, reaching a height of 30 to 40 feet at maturity.

Branches: The new growth and young branches are glabrous, non-fading golden-yellow (T., K., and G. No. 2 ic) with large black winter buds. Branches are especially colorful during the winter in the absence of the leaves, and may be cut for use in indoor decorative arrangements.

Foliage: Opposite compound with from 7 to 11 sessile leaflets ovate lanceolate in shape, 2 to 4 inches long, with a finely serrated margin.

Foliage Color: Light green (T., K., and G. No. 24 ng) upper surface, and paler green (T., K., and G. No. 24½ ic) lower surface, changing colors during the summer to a strong vibrant golden hue (T., K., and G. No.1½ ic) which remains until leaf drop.

Flowers: Bi-sexual, small greenish white male flowers are borne in panicles and are inconspicuous.

Fruit: None.

I claim:

A new and distinct variety of ash tree, substantially as herein shown and described, characterized particularly as to novelty by its rapid growth rate, medium size, attractive rounded shape at maturity, its cleanness as a result of the lack of winged seed production, its unusual golden bark on young branches and twigs, and light green foliage which changes to golden yellow in August and remains until leaf drop.

No references cited.